US010151645B2

(12) United States Patent
Yeap et al.

(10) Patent No.: US 10,151,645 B2
(45) Date of Patent: Dec. 11, 2018

(54) ARRANGEMENT AND METHOD FOR THE SYNCHRONOUS DETERMINATION OF THE SHEAR MODULUS AND OF THE POISSON'S NUMBER ON SAMPLES OF ELASTICALLY ISOTROPIC AND ANISOTROPIC MATERIALS

(71) Applicant: Fraunhofer-Gesellschaft zur Foerderung der angewandten Forschung e.V., Munich (DE)

(72) Inventors: Kong Boon Yeap, Dresden (DE); Malgorzata Kopycinska-Mueller, Dresden (DE); Ehrenfried Zschech, Moritzburg (DE); Martin Gall, Dresden (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 792 days.

(21) Appl. No.: 14/474,850

(22) Filed: Sep. 2, 2014

(65) Prior Publication Data

US 2015/0066394 A1 Mar. 5, 2015

(30) Foreign Application Priority Data

Sep. 3, 2013 (DE) ........................ 10 2013 014 807

(51) Int. Cl.
*G06F 11/30* (2006.01)
*G01L 1/00* (2006.01)
(Continued)

(52) U.S. Cl.
CPC ................. *G01L 1/00* (2013.01); *G01N 3/24* (2013.01); *G01N 3/46* (2013.01); *G01Q 60/366* (2013.01); *G01N 2203/0069* (2013.01)

(58) Field of Classification Search
CPC ........................................................ G01N 3/24
See application file for complete search history.

(56) References Cited

U.S. PATENT DOCUMENTS

| 6,339,956 B1 * | 1/2002 | Huinink | B60C 15/06 |
| | | | 152/152.1 |
| 6,339,958 B1 | 1/2002 | Tsui et al. | |
| 2010/0108884 A1 * | 5/2010 | Lou | G01N 3/42 |
| | | | 250/311 |

FOREIGN PATENT DOCUMENTS

WO WO 2013/108208 A1 7/2013

\* cited by examiner

*Primary Examiner* — Phuong Huynh
(74) *Attorney, Agent, or Firm* — Jacobson Holman, PLLC.

(57) ABSTRACT

The invention relates to an arrangement and to a method for the synchronous determination of the shear modulus and of the Poisson's number on samples of elastically isotropic and anisotropic materials. In the arrangement, an indenter is movable in parallel with its longitudinal axis (A) in the direction of the surface of a sample such that a force action is exerted on the material by its tip. The force can be determined by a device for measuring this force and the indenter is additionally deflected in translation along at least one further axis. The longitudinal axis (A) of the indenter is aligned at an angle ≠90° with respect to the surface of the sample and the indenter carries out an upward movement and a downward movement. In this respect, a device is present for calculating the shear modulus G and the Poisson's number v from the contact stiffness k determined in this manner, from the acting normal force P, from the indentation modulus $M_S$ and from the shear modulus-related parameter $N_S$ of the sample while taking account of the respective angle θ.

12 Claims, 6 Drawing Sheets

(51) Int. Cl.
*G01Q 60/36* (2010.01)
*G01N 3/46* (2006.01)
*G01N 3/24* (2006.01)

ARRANGEMENT AND METHOD FOR THE SYNCHRONOUS DETERMINATION OF THE SHEAR MODULUS AND OF THE POISSON'S NUMBER ON SAMPLES OF ELASTICALLY ISOTROPIC AND ANISOTROPIC MATERIALS

The invention relates to an arrangement and to a method for the synchronous determination of the shear modulus and of the Poisson's number on samples of elastically isotropic and anisotropic materials, in this respect, a sample can be formed completely from the material. A sample can, however, also be coated with the material. Such materials are, for example, silica glass, organosilica glass (OSG), copper, iron and many more. In this respect, a local resolution in the nanometer range can be achieved.

An atomic force microscope (AFM) or an indenter can be used in the invention in conjunction with a force measuring device by which a force acting on the sample can be determined. At least the tip of the indenter has a higher stiffness than the stiffness of the material for which the shear modulus and the Poisson's number are to be determined. Some nanoindenters and AFM-based processes can determine the local stiffness k of a sample (see patent and publication by Asif and Wahl). The indenter can in this respect be moved in three axial directions to allow a spatial resolution in the measurement. When forming an indentation in the surface of the sample, it is, however, generally moved perpendicular with respect to the surface of the sample so that generally an angle of 90° is observed between the longitudinal axis of the indenter, or of its force action vector, and the surface of the sample. However, neither the shear modulus G nor the Poisson's number v can be determined using such a design and such a procedure.

The measurement of such elastic constants using mechanical contact-based techniques is, however, usually limited to the normal contact stiffness determination by deforming a sample out of the normal direction. The measurement of the lateral contact stiffness is difficult since the machine stiffness is as a rule not sufficiently large and complicated peak contact geometries have to be taken into account by indenters. Without the measurement of the lateral stiffness, the shear modulus and the Poisson's number cannot be determined experimentally by mechanical examinations.

Empirical determinations of the Poisson's number v based on experience can admittedly be used for the compressive stress calculation. These measurements are, however, very difficult and complex and/or expensive to carry out, which in particular applies to nanostructures and microstructures.

Acoustic techniques can be used for determining the E modulus and Poisson's number v for regions close to the surface when the values of the density and the thickness of a thin film are known. The principle is based on the determination of the transverse and longitudinal sound wave speeds which are conducted along the sample surface. The acoustic microscope technique can be used with good results for determining the average properties. The properties of individual microscale structures can, however, not be determined in this manner.

The mathematical treatment of indentation load displacement data with acting normal forces was previously used to obtain the Poisson's number v of coatings and of thin films. These results can, however, not be supported on a direct measurement of the lateral contact stiffness. Such mathematical processes can therefore not sufficiently resolve the properties of complex microscale and nanoscale structures.

A contact resonance atomic force microscope (CR-AFM) and a multidimensional nanoindentation (MD-NI) can be used for determining the lateral contact stiffness. The bending and torsion contact resonance frequencies can be measured simultaneously using a CR-AFM. Calculations of the lateral contact stiffness and their interpretation with respect to the geometry of the peak are, however, difficult to carry out. In addition, these calculated parameters require a continuous monitoring since they are not constant during the measurements. In the MD-NI process, the lateral contact stiffness is determined by the exertion of force actions in the normal direction and in the lateral direction while a diamond indenter acts perpendicularly on a sample. The lateral contact stiffness can be determined by analysis of the lateral force displacement data, by static load and by superimposed load. The lateral force which occurs in this process not only effects a lateral displacement of the sample, but a bending of the indenter shaft rather also occurs. The laterally acting force must be so small that an exact lateral contact stiffness value can be obtained. The resolution of the force and displacement sensor limits the use of the MD-NI process.

It is therefore the object of the invention to provide possibilities for the determination of elastic constants, in particular the shear modulus and Poisson's number on materials having elastically isotropic and anisotropic properties, which achieve sufficient measurement accuracy.

This object is achieved in accordance with the invention by an arrangement having the features of claim 1. In this respect, it is also possible to work using a method in accordance with claim 6. Advantageous embodiments and further developments of the invention can be realized using features designated in subordinate claims.

In the arrangement in accordance with the invention, an indenter is movably arranged in parallel with its longitudinal axis A in the direction of the surface of a sample 2. The movement in this case takes place such that the tip of the indenter exerts a force action on the material. The exerted force is determined by means of a device for measuring this force. The indenter can in this respect be additionally deflected in translation along at least one further axis. In this movement, the tip of the indenter is guided along this axis over the surface of the sample.

It is essential to the invention that the longitudinal axis A of the indenter is aligned at an angle ≠90° with respect to the surface of the sample. An angular range θ between 1° and 5° is preferred.

In this respect, the longitudinal axis of the indenter can exert a force action on an inclined surface due to the topography of the sample. The angle θ≠0 can, however, also be achieved by a corresponding inclination of the surface of the sample with respect to the vertical and to the horizontal.

There is also the possibility of modifying or setting the angle between the longitudinal axis (A) of the indenter and the surface of the sample and then to repeat the measurement at an angle changed once or a multiple of times. A suitable adjustment drive can be present for this purpose, in the measurements, the respective inclination angle should be known and should be taken into account in the determination.

The indenter should be deflected in two opposite axial directions in translation along an axis on the surface of the sample by a movement to and fro. In this respect, the tip of the indenter can be moved along the surface upwards in one direction and downwards in the opposite direction, whereby a movement takes place once with an active compressive force and a movement takes place once in the opposite direction with an active tensile force. In this respect, the tip of the indenter should cover the distance of an identical path between two reversal points of the upward movement and of the downward movement.

This effect can, however, also be achieved if a surface of a sample is formed such that it has regions with different inclination alignments, such as is the case, for example, with a wedge shape. In this respect, the indenter tip can be moved downward and pulled at an inclined surface and can be pressed upward at an oppositely inclined surface. In this case, the inclination angle can also be of the same amount with respect to the vertical.

The vertical contact stiffness is measured simultaneously with the movement of the indenter tip on the inclined surface. The detailed method of measuring the contact stiffness is dependent on the instrument used to travel over the sample surface and differs for AFM-based applications and for nanoindenters. With the scanning probe microscopes and indenters which can be used in the invention, this is, however, easily possible due to their basic structure.

The shear modulus G and the Poisson's number v are calculated from the determined contact stiffness k, the acting normal force P, the indentation modulus $M_S$ and the shear modulus-related parameter $N_S$ of the sample while taking account of the respective angle θ. A suitable device is present for this purpose.

It is advantageous if the tip of the indenter can be moved along its longitudinal axis in an oscillating manner, preferably in a sinusoidal oscillating manner.

For a contact stiffness determination in the normal force direction, an indenter or a tip of an atomic force microscope at a high frequency between 100 Hz and 200 Hz for an indenter and between 10 kHz to 3.5 MHz for an atomic force microscope can be moved over a flat surface in an oscillating manner. In this respect, a simple experimental method, which can be called an inclined surface scan examination, can be used for determining the lateral contact stiffness.

In this respect, the scanning of an indenter tip at a surface of the sample inclined with respect to the longitudinal axis of the indenter by an angle not equal to 90° is important. An additional movement advantageously takes place in two opposite directions or inclination directions. The movement in this respect takes place in an upward movement and in a downward movement or by a movement in a compressive force direction and by a movement in a tensile force direction along the surface of the sample inclined accordingly with respect to the longitudinal axis of the indenter.

The tip of the indenter can have a symmetrical ($\alpha_1 = \alpha_2$) or an asymmetrical ($\alpha_1 \neq \alpha_2$) geometry. The respective geometry of the tip should be taken into account. If the tip is moved along an inclined surface, the dynamic displacement has two components, one in the normal force direction and once in the lateral direction. A higher force (piezo scanning force) $P_{lateral-up}$ is exerted to move the tip of the indenter in the direction of the inclined surface upward or with a compressive force. The force ($P_{lateral-down}$) in the opposite downward direction or in the tensile force direction is smaller.

The shear modulus G and the Poisson's number v are calculated from the determined contact stiffness k, the indentation modulus $M_S$ and the shear modulus-related parameter $N_S$ of the sample while taking account of the respective angle θ. The equations suitable for this will be named in the following.

Using the invention, the shear modulus G and the Poisson's number v can be determined with a resolution in the nanometer range by movement of a sharp indenter tip in an upward and downward direction or with an acting compressive force and tensile force in dependence on the alignment of the respective inclined surface and of the direction of movement of the indenter tip along the surface of a sample.

Using the invention, the shear modulus G and the Poisson's number v can be determined by a simultaneous measurement. A complete set of elastic constants can advantageously be determined for different substances/materials. Nanoscale structures can be taken into account and the procedure for the determination can be simplified.

The values which can be determined of shear modulus G and Poisson's number v are properties of substances/materials and can be utilized for the simulation and calculation of compressive stress distributions in a product such as integrated circuits, micromechanical elements, screen applications and many more.

The invention will be explained in more detail by way of example in the following.

There are shown.

Figure 1:
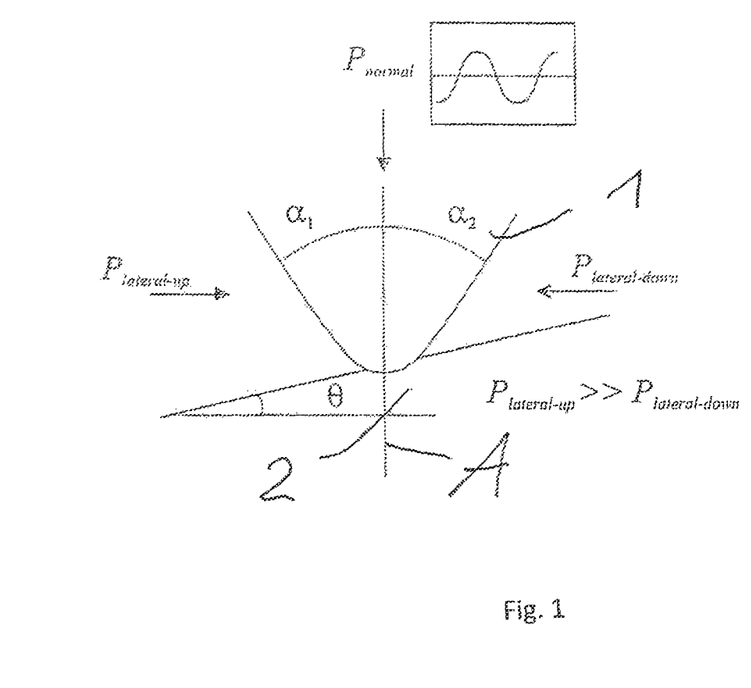
FIG. 1 in schematic form, a tip of an indenter movable on a surface of a sample inclined at an angle θ.

To demonstrate the operating principle, a wedge indenter was utilized to form a recess in a surface of a sample 2 of silica glass. The sample 2 has two inclined surfaces arranged opposite one another. They are an inclined surface I and a further inclined surface II. The gradient of the inclined surfaces tan θ can be changed or influenced by a change of the plastic deformation and depth of the formed wedge indentation in the sample 2. The angle θ is in this respect the angle between the horizontal and the respective inclined surface when the longitudinal axis A of the indenter 1 is aligned vertically. In FIG. 1, the angle θ is the angle between the horizontal and the inclined surface of the sample 2. The longitudinal axis A of the indenter 1 is aligned vertically in this representation so that the indenter 1, as indicated by the arrow, is moved in this direction onto the surface of the sample to exert a force action there. It is furthermore pointed out that the force action can be exerted as a sinusoidal normal force $P_{normal}$ in an oscillating manner and lateral forces $P_{lateral-up}$ and $P_{lateral-down}$ act additionally in an additional movement.

Figure 2:
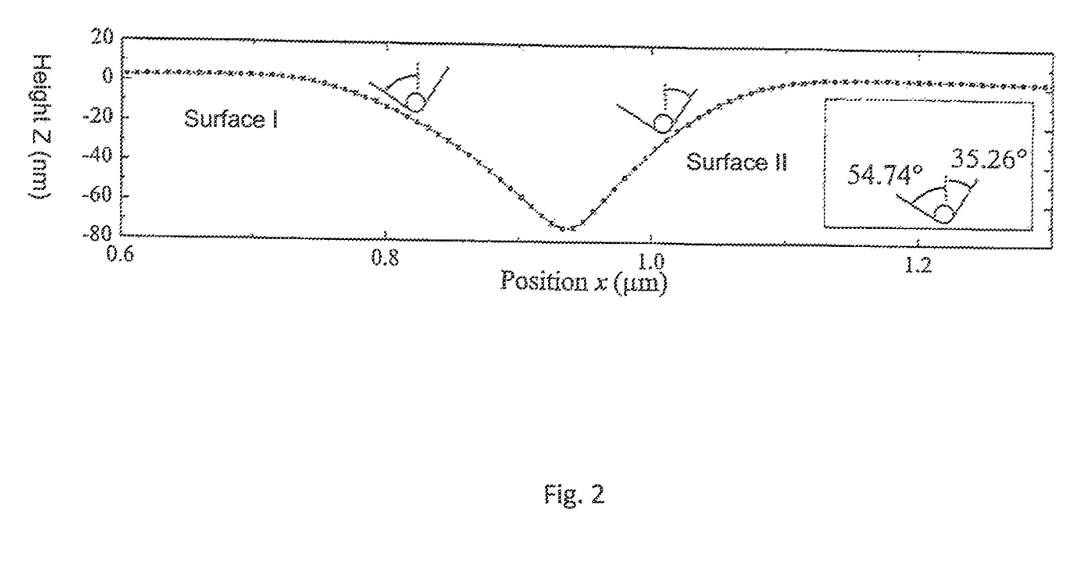
FIG. 2 a line scan which has been detected with a hexahedral tip of an indenter along the topography of a surface of a sample with a wedge shape in a downward and upward movement.

FIG. 2 shows a line scan which has been detected using a hexahedral tip of an indenter 1 along the topography of the wedge indentation. The tip is in contact with the sample 2 at the inclined surface I of the edge between two adjacent surfaces, of the hexahedral tip of the indenter 1. The flat surface of the hexahedral tip is in contact with the sample 2 at the inclined surface II when the indenter tip is moved upward from left to right. The indenter tip moves downward at the inclined surface I and upward at the inclined surface II. When the indenter tip is moved in the opposite direction, that is from right to left, it moves downward at the inclined surface II and upward at the inclined surface I.

Figure 3:
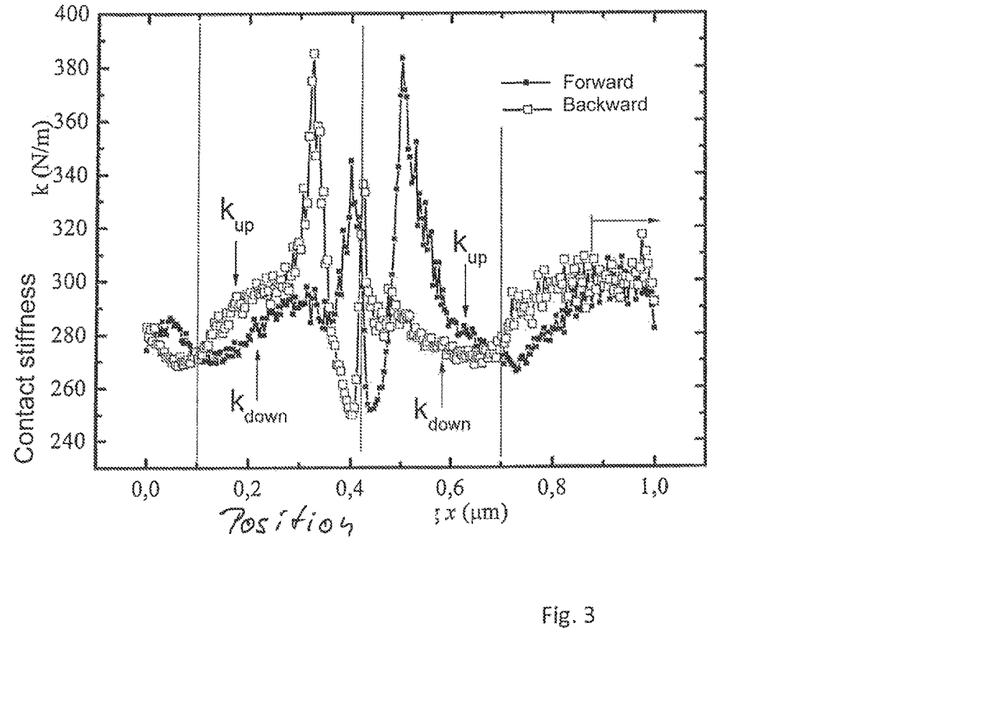
FIG. 3 a change of the values of the vertical contact stiffness determined as a function of the indenter position along the same path as explained in FIG. 2.

FIG. 3 shows changes in the values of the vertical contact stiffness as a function of the indenter position along the line scan. The contact stiffness is detected during the movement. As a result of the asymmetry of the geometry of the indenter tip and of the differences of the forces in the upward movement and downward movement respectively, the contact stiffness can be determined at differently profiled surfaces on a forward and backward movement or an upward and downward movement.

The difference between the calculated contact stiffnesses in the upward and downward movement is proportional to the displacement of the sample surface in the lateral direction and in the normal direction. The difference of the forces acting on the tip in the lateral direction and in the normal direction during the upward and downward movement also behaves in this manner. If the lateral displacement for the downward movement is small, the lateral contact stiffness can be determined using the following equations:

$$m*k_{lat}=|(k_{down}*k_{up})/(k_{up}-k_{down})|, \quad (1)$$

$$m=f(P_{normal},\mu,\theta), \quad (2)$$

where $k_{down}$ and $k_{up}$ are the contact stiffness in the normal force direction for the downward movement and for the upward movement and $k_{lat}$ is the lateral contact stiffness. The correction factor m is a function of the normal force $P_{load}$, $\mu$ is the coefficient of friction and $\theta$ is the inclination angle of the inclined surfaces with respect to the horizontal or is the complementary angle to the angle between the inclined surface of the sample and the longitudinal axis of the indenter 1.

The normal force $P_{normal}$ can be an experimentally defined constant (in the range between 1 µN to 3 µN) and µ is a constant for the respective material when m is a variable parameter which is dependent on the tip alignment of the indenter 1 and on the inclined surface(s). After the lateral contact stiffness $k_{lat}$ has been determined, the reduced shear modulus $G_R$ can be determined. The reduced shear modulus which takes account of the tip of the indenter 1 and the sample 2 can be determined with $$G_R=k_{lat}/8a \quad (3)$$

$$G_R=m*G'_R \quad (4)$$

where G'R is the effective shear modulus without the correction factor m and a is the contact radius which has been determined for a predefined indentation depth of the tip calibration function.

The Poisson's number v can be determined by $$v=(M_S-4N_S)/(M_S-2N_S), \quad (5)$$

$$1/E_R=((1/M_S)+((1-v^2_{tip})/E_{tip})), \quad (6)$$

$$1/G_R=((1/N_S)+((2-v_{tip})/G_{tip})), \quad (7)$$

for elastically isotropic materials. Here, $E_{tip}$, $G_{tip}$ and $v_{tip}$ are the elastic properties of the indenter tip. $E_R$ is the reduced E modulus of the combination of indenter tip and sample in the measurement in the normal force direction, $M_S$ is the indentation modulus ($M_S=E_S/(1-v_S^2)$, $N_S$ is the shear modulus-related parameter of the sample ($N_S=G_S/(2-v_S)$).

Figure 4:
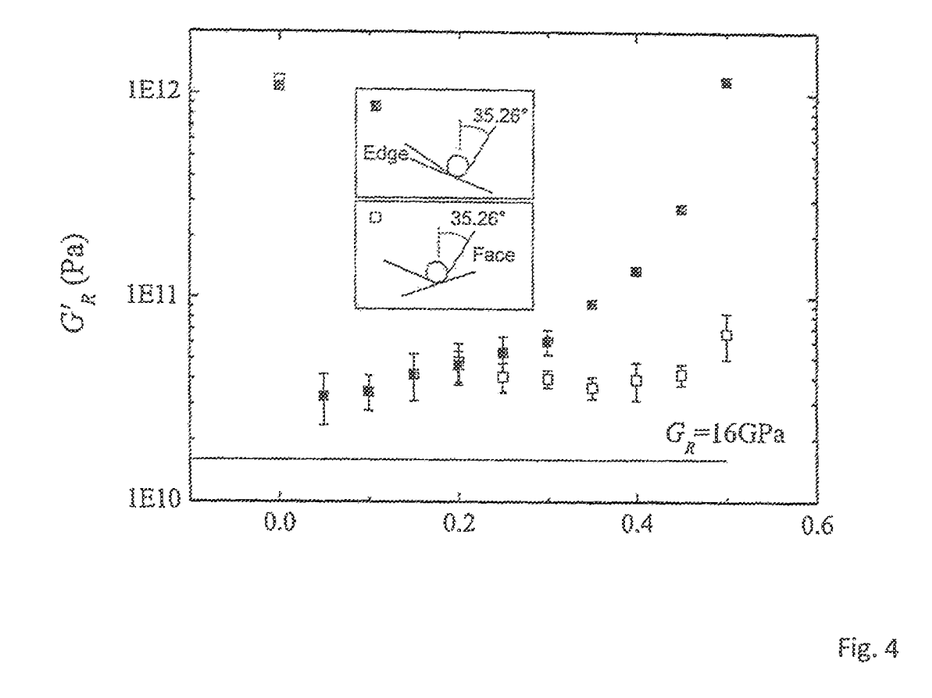
FIG. 4 a diagram of determined effective reduced shear moduli $G'_R$ of a sample of silica glass applied over the topographic gradient tan θ.

FIG. 4 shows the reduced shear modulus G'$_R$ of silica glass, applied over the topographic gradient tan θ. The filled squares in the diagram reproduce the results of the movement of the edge of the hexahedral tip of the indenter 1 along the inclined surface I and the non-filled squares reproduce the results on the movement with the surface of the hexahedral indenter tip along the inclined surface II on a movement from left to right.

It can be recognized in this respect that the orientation of the hexahedral indenter tip and the gradient of the inclination angle θ have a great influence on the reduced shear modulus G'$_R$. The value of the correction factor m can be determined using the equation (4) and can be used in equations (1, 3) to determine the shear modulus $G_R$. With knowledge of the values for $E_R$ and $G_R$ for the respective sample, the Poisson's number v can be determined using the equations (5 to 7).

Figure 5:
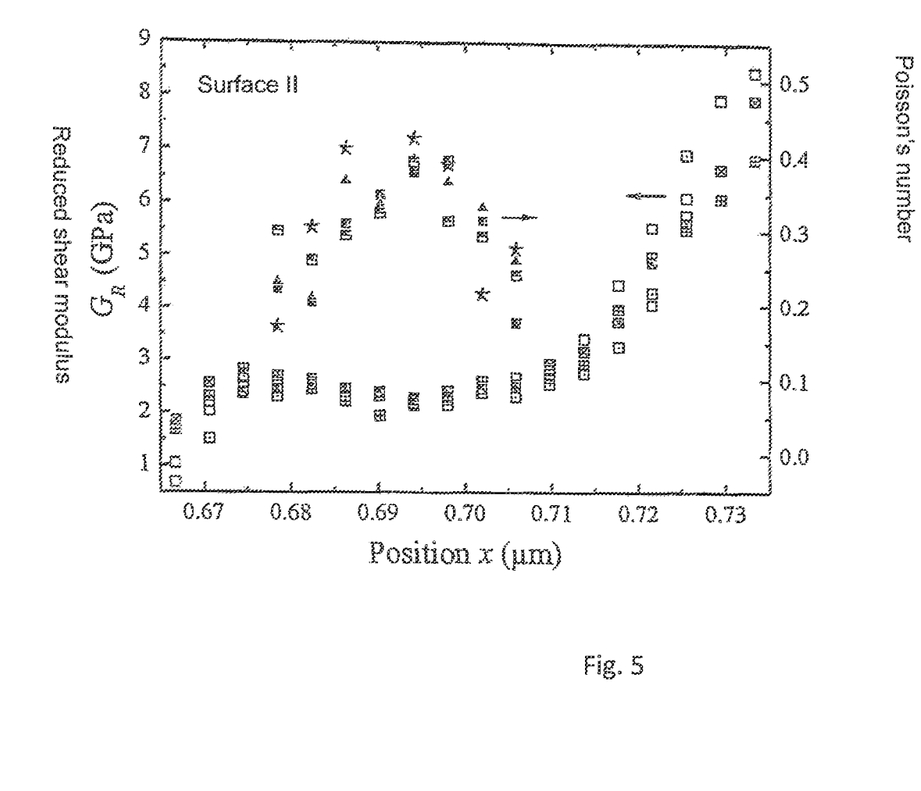
FIG. 5 the results obtained at an inclined surface II for the determined reduced shear modulus and the Poisson's number at different positions, with the surface II being inclined such that the tip of the indenter carries out an upward movement.

The procedure as described above can be used with dense organosilica glass (OSG) thin films. A wedge indentation having the inclined surfaces I and II, as shown in FIG. 2, can in this respect be formed in the surface of the OSG film. The reduced shear modulus $G_R$ and the Poisson's number v can be calculated using the equations (1 to 7). FIG. 5 shows the results obtained at the inclined surface II. In this respect, the value of the shear modulus $G_R$ is at 2.45±0.21 GPa and the value for the Poisson's number v at 0.31±0.08. Both values determined in this manner in this respect lie very close to the expected values of $G_R$=2.86 GPa and v=0.3. The shear modulus G and the Poisson's number v can be determined sufficiently exactly using the invention.

Figure 6:
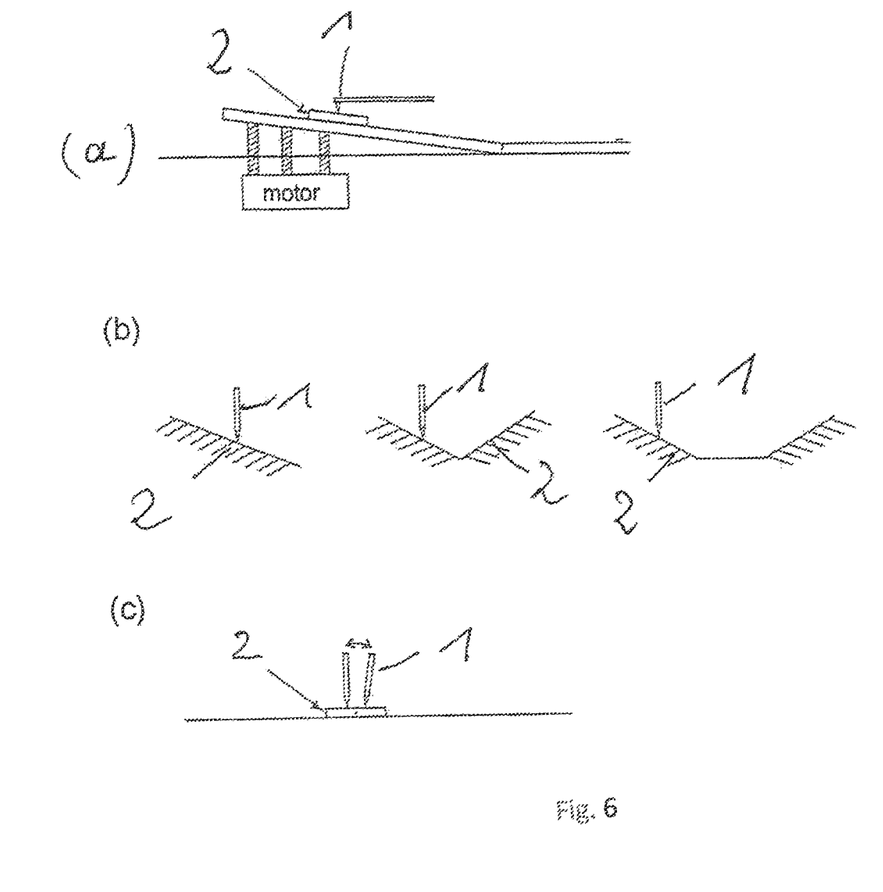
FIG. 6 examples for the inclination possibilities of the indenter and the sample surfaces.

FIG. 6 shows examples for arrangements in accordance with the invention. In the example shown in FIG. 6a, an arrangement is shown in which an inclined surface can be adjusted in its inclination angle θ. FIG. 6b gives examples with mechanically or chemically formed inclined surfaces which can also be formed as a wedge-shaped recess. In FIG. 6c, an arrangement with an adjustable Inclination angle of an indenter 1 is shown.

The longitudinal indenter axis A is not aligned perpendicular to the surface of the sample 2 during the obliquely inclined movement of the indenter tip, as is the case with the prior art.

The inclination angle θ of the surface of a sample can lie in the range 1° to 5°; the correspondent tangent values can be seen from the diagram shown in FIG. 4.

In a further example, the shear modulus and the Poisson's number were determined at a sample of organosilica glass with M=12 GPa.

In this respect, a topographic determination of the of the lateral contact stiffness of the sample was made. An indenter having a tip at which corners and edges are formed was used. The lateral contact stiffness was determined separately in each case on an upward movement and downward movement which has been carried out on the identical path distance between two reversal points. In this respect, a force of 1 µN was exerted on the indenter in the axial direction of its longitudinal axis A.

The apparent lateral contact stiffness k'$_{lat}$ can be determined using the equation $$k'_{lat}=(k_{down}*k_{up})/(k_{down}-k_{up}) \quad (8)$$

To determine the effective reduced shear modulus, the contact surface $A_C$ of the indenter tip on the sample was first determined with $A_C=\pi(k*/2 E*)$ where E* is the reduced E modulus of the sample of around 13 GPa.

Using the contact surface $A_C$ thus determined, the contact radius of the indenter tip on the sample can be calculated and can be determined for determining the apparent reduced shear modulus G'$_r$, as G'$_r$? k'$_{lat}$/8a.

The surface gradient can be calculated from this topography information.

While taking account of the asymmetry of the indenter tip, the sides which contact the sample surface on the upward and downward movement have different geometrical designs so that different tip geometries have to be taken into account in the respective movements. This has the result that respective different correction factors m have to be taken into account for the upward and downward movement. They can be determined as reference values at a quartz sample.

The reduced shear modulus can be calculated from the apparent shear modulus $G'_R$ with $G_R=m*G'_R$. A mean value can be calculated using the matrix for values at different positions thus obtained, with extreme values having been excluded from the calculation. A reduced shear modulus $G_R$ of 2.04 GPa±0.5 GPa was determined at 886 positions for this sample. The Poisson's number v can be calculated using $v=(M_S-4 N_S)/(M_S-2 N_S)$, wherein $M_S=12$ GPa and $N_S$ have been calculated with $N_S=((1/G_R)-3.62^{-12} Pa^{-1}))^{-1}$.

The mean value of the Poisson's number v was able to be determined with 0.46±0.2.

With knowledge of the Poisson's number v and of the reduced shear modulus $G_R$, the value of the shear modulus can be calculated with $G_S=N_S (2-v)$. For the sample of organosilica glass it amounted to G=3.3 GPa±1.3 GPa.

A determination of the shear modulus and of the Poisson's number can also take place in this form for other materials than the organosilica glass.

The invention claimed is:

1. A method for the synchronous determination of the shear modulus (G) and of the Poisson's number (v) of an elastically isotropic or anisotropic material, comprising the steps of
    moving an indenter in a normal direction parallel to the longitudinal axis of the indenter against a surface of the material at an angle with the surface not equal to 90°, wherein the indenter has a tip aligned with the longitudinal axis, through which tip the indenter exerts normal force ($P_{normal}$) against the material surface, while
    moving the indenter tip in a lateral direction upward and downward, sequentially, exerting lateral-up force ($P_{lateral-up}$) and lateral-down force ($P_{lateral-down}$), respectively, against the material surface,
    measuring $P_{normal}$,
    determining contact stiffness (k), indentation modulus ($M_S$), and shear modulus-related parameter ($N_S$) of the material, and
    calculating the shear modulus (G) and the Poisson's number (v) of the material based on $P_{normal}$, k, $M_S$, $N_S$, and θ, wherein θ is the acute angle formed between the surface of the material and the indenter longitudinal axis.

2. The method of claim 1, wherein the indenter tip moves upward and downward along an identical path between two reversal points during reciprocating motion.

3. The method of claim 1, wherein the indenter tip moves parallel with the longitudinal axis in an oscillating manner with a constant amplitude exerting $P_{normal}$ against the material surface.

4. The method of claim 1, wherein the indenter tip moves parallel with the longitudinal axis in an sinusoidal oscillating manner with a constant amplitude exerting $P_{normal}$ against the material surface.

5. The method of claim 1, wherein θ is an angle in the range 1°-5°.

6. An arrangement, for performing the method of claim 1, comprising
    a) an indenter configured for
        i) moving in a normal direction parallel to the longitudinal axis of the indenter against a surface of a material at a contact angle with the surface not equal to 90°, wherein the indenter has a tip aligned with the longitudinal axis, through which tip the indenter can exert a normal force ($P_{normal}$) against the material surface, while
        ii) moving the indenter tip in a lateral direction upward and downward, sequentially, for exerting lateral-up force ($P_{lateral-up}$) and lateral-down force ($P_{lateral-down}$), respectively, against the material surface,
    b) a device, cooperating with the indenter, for measuring the $P_{normal}$, and
    c) a device for calculating the shear modulus (G) and the Poisson's number (v) of the material based on the $P_{normal}$, k, $M_S$, $N_S$, and θ.

7. The arrangement of claim 6, wherein the indenter is configured to effect a contact angle such that θ is an angle in the range 1°-5°.

8. The arrangement of claim 6, wherein the contact angle is adjustable.

9. The arrangement of claim 6, wherein the indenter is further configured for moving the indenter tip in a lateral direction upward and downward, sequentially, exerting lateral-up force ($P_{lateral-up}$) and lateral-down force ($P_{lateral-down}$), respectively, against the material surface.

10. The arrangement of claim 6, wherein the indenter is further configured for moving the indenter tip in a lateral direction upward and downward, sequentially, exerting lateral-up force ($P_{lateral-up}$) and lateral-down force ($P_{lateral-down}$), respectively, against the material surface along an identical path between two points of reversal.

11. The arrangement of claim 6, wherein the indenter is further configured for moving parallel longitudinal axis in an oscillating manner, such that the tip exerts $P_{normal}$ against the material surface in an oscillation matter, and for recording the contact stiffness during the movement.

12. The arrangement of claim 6, wherein the indenter is further configured for moving parallel longitudinal axis in a sinusoidal oscillation manner, such that the tip exerts $P_{normal}$ against the material surface in a sinusoidal oscillation manner, and for recording the contact stiffness during the movement.

* * * * *